(12) United States Patent
Brouillette et al.

(10) Patent No.: US 7,803,129 B2
(45) Date of Patent: Sep. 28, 2010

(54) NEEDLELESS SYRINGE FOR THE SUBCUTANEOUS INJECTION OF DROPLETS OF LIQUID SUBSTANCES

(75) Inventors: Martin Brouillette, Sherbrooke (CA); Stephane Dufresne, St. Jean de Matha (CA)

(73) Assignee: Societe de Commercialisation des Produits de la Recherche Appliquee-Socpra Sciences et Genie, S.E.C., Sherbrooke, Quebec (CA)

( * ) Notice: Subject to any disclaimer, the term of this patent is extended or adjusted under 35 U.S.C. 154(b) by 293 days.

(21) Appl. No.: 10/510,267

(22) PCT Filed: Apr. 4, 2003

(86) PCT No.: PCT/CA03/00516

§ 371 (c)(1),
(2), (4) Date: Mar. 14, 2005

(87) PCT Pub. No.: WO03/086510

PCT Pub. Date: Oct. 23, 2003

(65) Prior Publication Data

US 2005/0154369 A1 Jul. 14, 2005

(30) Foreign Application Priority Data

Apr. 5, 2002 (CA) .................................. 2380671

(51) Int. Cl.
*A61M 5/30* (2006.01)
(52) U.S. Cl. ........................... 604/68; 604/70; 604/131; 128/200.14; 128/200.21
(58) Field of Classification Search .................. 604/68, 604/70, 131, 140, 141, 143; 128/200.14, 128/200.18, 200.21–23; 12/200.21–23
See application file for complete search history.

(56) References Cited

U.S. PATENT DOCUMENTS 5,261,601 A * 11/1993 Ross et al. ................ 239/102.2

(Continued)

FOREIGN PATENT DOCUMENTS

FR 1041887 10/1953

(Continued)

OTHER PUBLICATIONS

Anno, "The Mechanics of Liquid Jets", 1977, pp. 57-61.

(Continued)

*Primary Examiner*—Kevin C Sirmons
*Assistant Examiner*—Deanna K Hall
(74) *Attorney, Agent, or Firm*—Fay Kaplun & Marcin, LLP (57) ABSTRACT

Described are a method and device for needleless injection of a liquid substance in the skin or other target tissue of a patient, in which droplets of the liquid substance are produced, and the droplets of liquid substance are directed toward the surface of the patient's skin or other target tissue at a velocity sufficiently high to inject the droplets of liquid substance in the patient's skin or other target tissue. The droplets of the liquid substance are accelerated toward the surface of the patient's skin or other target tissue in order to inject the accelerated droplets of liquid substance in the patient's skin or other target tissue. A high velocity jet of gas is produced, droplets of the liquid substance are produced and supplied in the high velocity jet of gas, the droplets of liquid substance are conveyed within the high velocity jet of gas, and the high velocity jet of gas is guided toward the surface of the patient's skin or other target tissue in order to inject the conveyed droplets of liquid substance in the patient's skin or other target tissue.

32 Claims, 6 Drawing Sheets

U.S. PATENT DOCUMENTS

| | | | |
|---|---|---|---|
| 5,630,796 A * | 5/1997 | Bellhouse et al. | 604/518 |
| 5,865,796 A | 2/1999 | McCabe | |
| 5,899,880 A | 5/1999 | Bellhouse et al. | |
| 5,954,689 A | 9/1999 | Poulsen | |
| 6,220,141 B1 | 4/2001 | Fitter et al. | |
| 6,689,095 B1 * | 2/2004 | Garitano et al. | 604/70 |
| 6,808,246 B2 * | 10/2004 | Long | 347/22 |
| 2002/0055712 A1 * | 5/2002 | Neracher | 604/143 |

FOREIGN PATENT DOCUMENTS

| | | |
|---|---|---|
| FR | 2800619 | 5/2001 |
| FR | 2804329 | 8/2001 |
| WO | 00/64514 | 11/2000 |

OTHER PUBLICATIONS

Bioject, Needle-free Injection Systems, htto://www.bioject.com/technology,html, 5 sheets.

Bioject, Needle-free Injection Systems, http://www.bioject.com/technology.html, 1 sheet.

The Advantajet, http://www.advantajet.com/mainsite.htm, 1 sheet.

Medi-Jector, http://mediject.com/how_it_works/index.htm, 1 sheet.

Powderject, Research & Development, http://www.powderject.com/, 2 sheets.

* cited by examiner

__NEEDLELESS SYRINGE FOR THE SUBCUTANEOUS INJECTION OF DROPLETS OF LIQUID SUBSTANCES__

FIELD OF THE INVENTION

The present invention relates to a method, device and needleless syringe for the subcutaneous injection of droplets of liquid substances in the skin or other target tissue of a patient.

BACKGROUND OF THE INVENTION

U.S. Pat. No. 5,899,880 granted to Bellhouse et al. on May 4, 1999 and U.S. Pat. No. 5,865,796 (McCabe) issued on Feb. 2, 1999 relate to devices for the high velocity injection of medicinal powders through the skin or other target tissue of a patient by means of high pressure gas.

More specifically, U.S. Pat. No. 5,899,880 describes a needeless syringe capable of accelerating the medicine to speeds sufficient to obtain the desired therapeutic effect. A company, Powderject Research Limited in the United Kingdom and Powderject Vaccines, Inc. in the United States, has been founded to exploit that concept.

U.S. Pat. No. 5,865,796 describes an essentially similar device, developed for the benefit of the same company. This device is destined to a usage in laboratory, for injecting genetic material.

The two above devices are designed for use with a medicine under the form of powder. They accelerate an inert gas by means of a supersonic gas flow.

The following companies already commercialize needleless syringes:

Powderject (www.powderject.com) uses a supersonic gaseous flow to accelerate microscopic particles in order to inject these particles into the skin or other target tissue of a subject;

Bioject (www.bioject.com) uses a micro-jet of high pressure liquid for the needleless penetration of the skin or other target tissue of a subject;

Advantajet (www.advantajet.com) uses a micro-jet of low pressure liquid, this system being optimized for insulin;

Mediject (www.mediject.com) uses an insulin injection system similar to that of Advantajet; and Many other companies exploit the concept of high pressure liquid jet for the needleless injection of liquids.

SUMMARY OF THE INVENTION

According to the present invention, there is provided a method for needleless injection of a liquid substance in the skin or other target tissue of a patient, comprising producing droplets of the liquid substance, and directing the droplets of liquid substance toward the surface of the patient's skin or other target tissue at a velocity sufficiently high to inject the droplets of liquid substance into the patient's skin or other target tissue.

The present invention also relates to a method for needleless injection of a liquid substance in the skin or other target tissue of a patient, comprising producing droplets of the liquid substance, and accelerating the droplets of liquid substance toward the surface of the patient's skin or other target tissue in order to inject the accelerated droplets of liquid substance into the patient's skin or other target tissue.

According to the present invention, there is also provided a method for needleless injection of a liquid substance in the skin or other target tissue of a patient, comprising producing a high velocity jet of gas, producing droplets of the liquid substance and supplying the droplets of liquid substance in the high velocity jet of gas, conveying the droplets of liquid substance within the high velocity jet of gas, and guiding the high velocity jet of gas toward the surface of the patient's skin or other target tissue in order to inject the conveyed droplets of liquid substance into the patient's skin or other target tissue.

The present invention further relates to a device for needleless injection of a liquid substance in the skin or other target tissue of a patient, comprising means for generating droplets of the liquid substance, and means for directing the droplets of liquid substance toward the surface of the patient's skin or other target tissue at a velocity sufficiently high to inject the droplets of liquid substance into the patient's skin or other target tissue.

According to the present invention, there is further provided a device for needleless injection of a liquid substance in the skin or other target tissue of a patient, comprising a generator of droplets supplied with the liquid substance, and a droplet accelerator for accelerating the droplets of liquid substance toward the surface of the patient's skin or other target tissue in order to inject the accelerated droplets of liquid substance into the patient's skin or other target tissue.

The present invention still further relates to a device for needleless injection of a liquid substance into the skin or other target tissue of a patient, comprising means for producing a high velocity jet of gas, means for producing droplets of the liquid substance, means for supplying the droplets of liquid substance in the high velocity jet of gas whereby the droplets of liquid substance are conveyed within the high velocity jet of gas, and means for guiding the high velocity jet of gas toward the surface of the patient's skin or other target tissue in order to inject the conveyed droplets of liquid substance in the patient's skin or other target tissue.

Still further according to the present invention, there is provided a needleless syringe for injecting a liquid substance in the skin or other target tissue of a patient, comprising a generator of high velocity jet of gas, and a generator of droplets supplied with the liquid substance, wherein:

the generator of droplets comprises an outlet for supplying the droplets of liquid substance in the high velocity jet of gas, whereby the droplets of liquid substance are conveyed within the high velocity jet of gas; and the generator of high velocity jet of gas comprises a channel for guiding the high velocity jet of gas toward the surface of the patient's skin or other target tissue to thereby inject the conveyed droplets of liquid substance in the patient's skin or other target tissue.

The foregoing and other objects, advantages and features of the present invention will become more apparent upon reading of the following non restrictive description of illustrative embodiments thereof, given by way of example only with reference to the accompanying drawings.

DETAILED DESCRIPTION OF THE ILLUSTRATIVE EMBODIMENTS

The illustrative embodiments of the present invention will now be described with reference to the accompanying drawings.

The present invention enables the injection of liquid substances, under the form of droplets, in the skin or other target tissue of a patient without directly perforating the skin or other target tissue as this is the case when a syringe with a needle is used. The liquid substances of concern may comprise, in particular but not exclusively, vaccines, anaesthetics, medicines, hormones, genetic compounds, etc. The small size of the droplets and the speed of these droplets as generated by the needleless syringe allow the liquid substances to penetrate the skin or other target tissue of the patient and reach a specific tissue target.

More specifically, sufficiently small droplets are generated and accelerated to a sufficiently high velocity to allow these droplets to penetrate the patient's skin or other target tissue and thereby produce the desired medical effect. The advantages of such an approach over needles are obvious; the three main advantages are:

- the increase in efficiency of the treatment, by targeting the desirable cells and tissues, more specifically but not restricted to, in the epidermis and dermis;
- the reduction of the risk of infection; and
- almost complete elimination of patients' pain and fear.

First Illustrative Embodiment of the Needleless Syringe

Figure 1:
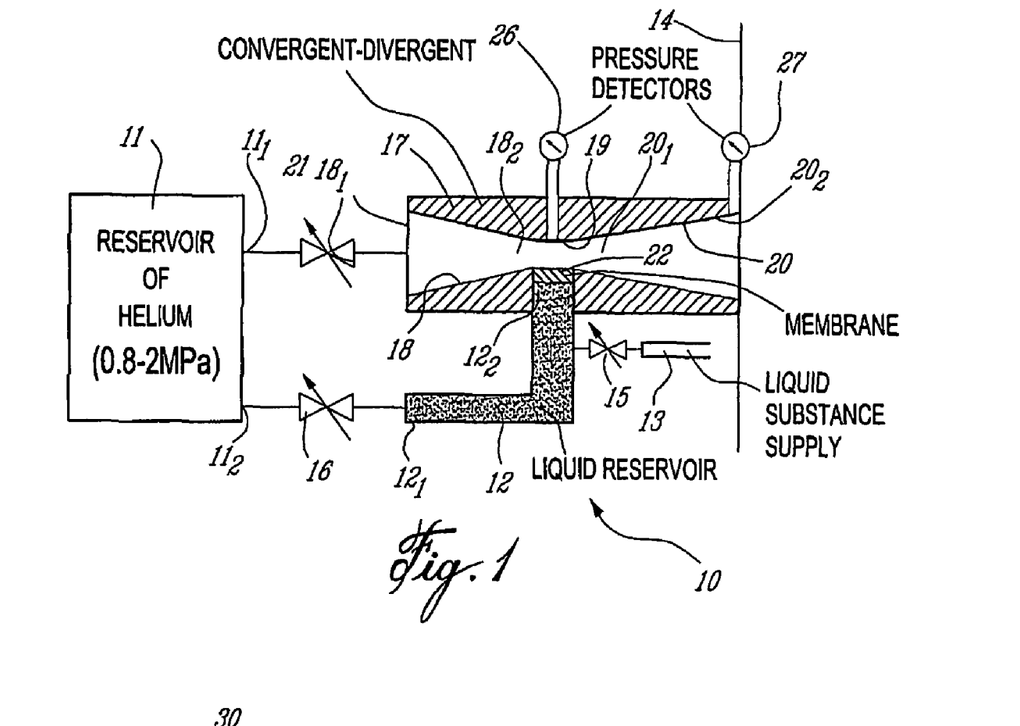
FIG. 1 is a schematic diagram illustrating the structure and operation of a first illustrative embodiment of needleless syringe in accordance with the present invention.

Referring to FIG. 1, the first illustrative embodiment of needleless syringe 10 comprises a reservoir 11 containing pressurized gas. As a non limitative example, the pressurized gas comprises a high pressure inert gas such as helium at a pressure of 0.8 to 2 MPa.

The needleless syringe 10 also comprises a reservoir of liquid 12 in which the liquid substance to be injected in the patient's skin or other target tissue 14 is supplied from a liquid substance supply 13 through a valve 15. The quantity of liquid substance will depend, in particular but not exclusively, on the required dosage. The reservoir 12 is L-shaped and comprises a first lower free end $12_1$ connected to an outlet $11_2$ of the reservoir 11 of pressurized gas through a valve 16.

The needleless syringe 10 further comprises a convergent-divergent 17 comprising serially interconnected convergent 18, throat 19 and divergent 20.

The convergent 18 comprises an end $18_1$ of larger diameter connected to an outlet $11_1$ of the reservoir 11 of pressurized gas through a valve 21. The convergent 18 also comprises an end $18_2$ of smaller diameter connected to one side of the throat 19.

The L-shaped reservoir 12 comprises a second upper end $12_2$ communicating with the throat 19 through a perforated membrane 22, for example a metallic or polymeric membrane 22 formed with at least one micro-orifice.

The divergent 20 comprises an end of smaller diameter $20_1$ connected to the other side of the throat 19. Finally, the divergent 20 comprises a free end $20_2$ of larger diameter which is open and, in operation, applied next to the surface of the skin or other target tissue 14 of the patient directly or through a spacer/silencer (not shown in FIG. 1).

The illustrative embodiment of needleless syringe 10 generally comprises two systems:

- a first system for generating droplets (generator of droplets) of given small size at a pre-selected flow rate; and
- a second system for accelerating the droplets (droplet accelerator) at a pre-selected velocity while directing these droplets toward a predetermined location of the surface of the skin or other target tissue.

First System for Generating Droplets:

Referring to FIG. 1 of the appended drawings, the first system for generating small droplets of given size at a pre-selected flow rate will now be described.

As illustrated in FIG. 1, when the valve 16 is opened, gas under pressure is supplied from the outlet $\mathbf{11}_2$ of the gas reservoir 11 to the inlet $\mathbf{12}_1$ of the liquid reservoir 12. The pressure of the gas in the reservoir 12 forces the liquid substance from the reservoir 12 through the micro-orifice such as 23 (FIG. 4) of the perforated membrane 22. On the side of the membrane 22 opposite to the reservoir 12, a jet 24 is produced by the liquid substance flowing through the micro-orifice 23. This jet is then transformed into droplets such as 25 via natural flow instabilities caused by the surface tension of the liquid.

Although the example of perforated membrane 22 as illustrated in FIG. 4 comprises only one micro-orifice, it should be kept in mind that the number and diameter of the micro-orifices such as 23 are determined in relation to the intended application. Moreover, the rate of flow of the liquid substance through the membrane 22 will be determined in relation to the number and the size of the micro-orifices 23 through the membrane 22 as well as the applied pressure at the inlet $\mathbf{12}_1$ of the liquid reservoir 12. In this droplet generating system, the size of the droplets 25 is controlled by the diameter of the orifice 23. Usually, it is found that the droplet size is about twice the orifice size.

In the first illustrative embodiment, the system for producing the droplets 25 uses a perforated membrane 22 comprising at least one micro-orifice through which liquid substance is forced by means of a pressure exerted upstream of the membrane 22. Another example of system for producing microscopic droplets 25 of controllable size can use an ultrasonic atomizer, such as those used in ultrasonic humidifiers.

Second System for Accelerating the Droplets:

As a non-limitative example, the second system for accelerating the droplets 25 (droplet accelerator) comprises the reservoir 11 of pressurized gas, the valve 21 and the convergent-divergent 17 (FIG. 1).

In operation, opening of the valve 21 will cause a high velocity jet of gas from the outlet $11_1$ through the convergent 18, the throat 19 and the divergent 20, to convey the droplets 25 produced within the throat 19 and to inject these droplets 25 in the patient's skin or other target tissue 14. An advantage connected to the use of a convergent-divergent 17 is the production of an almost steady state supersonic jet of gas.

An alternative to the use of a convergent-divergent 17 to accelerate the droplets 25 is the use of a shock tube or an expansion tube for producing a generally non-stationary flow with a certain duration of steady state flow velocity.

According to another alternative, the system for accelerating the droplets 25 can use electrostatic acceleration. In that particular case, the droplets 25 are first electrically charged, for example through a frictional process. The charged droplets are then subjected to an electrostatic field created between two parallel plates. The two parallel plates can be perforated or not, and are disposed parallel to the injection target surface. Of course, potentials of opposite polarities are respectively applied to the parallel plates. A similar device would use a magnetic field or a combination of various electromagnetic fields to produce droplet acceleration.

According to a further alternative that will be described in more detail in the following description, the system for accelerating the droplets 25 can use direct injection of the liquid substance. For that purpose, a high speed jet of the liquid substance is produced upstream of a membrane formed with micro-orifices. The jet of liquid substance becomes unstable and is transformed into a train of droplets. In accordance with this alternative, the perforated membrane is positioned close to the injection target surface parallel thereto.

Accordingly, the present invention proposes different methods for producing droplets and different methods for accelerating these droplets. It will readily appear to those of ordinary skill in the art that several combinations of these different methods for producing the droplets and these different methods for accelerating these droplets can be implemented.

It should also be pointed out that, in the case of droplet accelerating systems using a droplet-conveying high velocity jet of gas, the droplets can be injected at different locations of the high velocity jet of gas, and that whatever the droplet producing method being used. For example, when a convergent-divergent 17 is used to produce the quasi steady-state high velocity jet of gas, the droplets can be introduced in this high velocity jet of gas upstream of the throat 19, downstream this throat 19, or directly within that throat 19 of the convergent-divergent 17.

Operation of the First Illustrative Embodiment of Needleless Syringe

The first illustrative embodiment of the needleless syringe 10 of FIG. 1 operates as follows:

- the valve 21 is opened to supply gas under pressure from the outlet $11_1$ of the reservoir 11 through the convergent-divergent 17 until a steady-state high velocity jet of gas is established through this convergent-divergent 17;
- the valve 16 is then opened to supply gas under pressure from the outlet $11_2$ of the reservoir 11 to the liquid reservoir 12 and thereby force liquid from the reservoir 12 through the above described at least one micro-orifice of the membrane 22;
- as described with reference to FIG. 4, passage of liquid substance though each micro-orifice such as 23 of the membrane 22 produces, on the side of the membrane 22 opposite to the reservoir 12, a jet such as 24 of liquid substance, this jet being transformed into droplets such as 25; and
- the droplets 25 are accelerated by the high velocity jet of gas established through the convergent-divergent 17, in particular through the throat 19, toward the patient's skin or other target tissue 14; it should be pointed out that, in the first illustrative embodiment of FIG. 1, the droplets are accelerated by the viscous forces generated by a difference in velocity between the gas jet and the droplets.

Although this is not required for the needleless syringe to operate, the valve 21 is advantageously opened before the valve 16 is opened to enable the establishment of a steady-state high velocity jet of gas through the convergent-divergent 17 before the droplets 25 are produced and introduced in this high velocity jet of gas. This ensures a uniform velocity of the droplets 25.

Since the velocity and the size of the droplets control the depth of penetration of these droplets through the skin or other target tissue of the patient, it is appropriate to optimize these two parameters in order to maximize the therapeutic efficiency for a particular liquid medical formulation.

The theory related to the first illustrative embodiment of the needleless syringe as illustrated in FIG. 1 has been developed and the resulting model shows that the velocity of the jet of gas produced in the convergent-divergent 17 essentially varies as a function of:

- the ratio between the pressure of the gas in the reservoir 11 and the pressure at the output, that is at the free end $20_2$ of the divergent 20;
- the thermodynamic properties of the gas in the reservoir 11, in particular the speed of the sound (which depends on the temperature) and the ratio of the specific heats of this gas; and
- the ratio of the inner cross-section of the throat 19 and the inner cross-section of the output (free end $20_2$) of the convergent-divergent 17;

and the velocity of the droplets 25 essentially varies as a function of:

- the size of the droplets;
- the viscosity of the gas used to convey the droplets;
- the axial length of the divergent 20; and
- the velocity profile of the gas in the convergent-divergent.

In an exemplary, non-limitative set-up of the first illustrative embodiment of the needleless syringe according to the present invention, the inner cross-section of the throat 19 is 50 $mm^2$, while the inner cross-section of the free end $20_2$ of the divergent 20 is 77 $mm^2$, for an area ratio of about 1.5.

With this ratio of cross-sections, a pressure of 410 kPa in the throat 19 and an output pressure of 101.3 kPa at the free end $20_2$ of the divergent 20, the output velocity of the gas at the free end $20_2$ of the divergent 20 is 800 m/s. These pressure values were measured by means of two pressure sensors 26 and 27 positioned as illustrated in FIG. 1.

Then, a volume of water of 1 cc was injected in the liquid reservoir 12 through the valve 15. The membrane 22 comprised six (6) micro-orifices such as 25 with an average diameter of 200 microns. To determine the size of the droplets 25, the mechanics of liquid jets was used; the theory [ANNO, J. N. (1977), The Mechanics of Liquid Jets, Lexington Book, p. 103] states that the diameter of the generated droplets are about two times larger that the diameter of the micro-orifice. Consequently, the resulting droplets 25 had a diameter of about 400 microns, which is relatively large.

In order to determine whether the droplets were susceptible to penetrate the skin or other target tissue of a patient, tests have been made on the skin or other target tissue of a subject. To better visualise the level of penetration, the droplets have also been coloured. As a result, it was observed that the droplets could penetrate the target skin or other target tissue at a depth of about 1 mm under the above conditions.

The above numerical example clearly shows that control of both the size of the droplets 25 through the diameter of the micro-orifices such as 23 of the membrane 22 and the speed of the droplets 25 through the properties of the high velocity jet of gas, the depth of penetration of the liquid substance through the subject's skin or other target tissue could be controlled with high accuracy and reliability.

Second Illustrative Embodiment of the Needleless Syringe

A second illustrative embodiment of needleless syringe is generally designated by the reference 30 in FIGS. 2, 3*a*, 3*b*, 3*c* and 3*d*.

Referring to FIG. 2, the second illustrative embodiment of the needleless syringe 30 comprises a reservoir 31 containing a pressurized gas. For example, the pressurized gas comprises a high pressure inert gas such as helium at a pressure located within the range of 0.8 to 2 MPa.

The needleless syringe 30 also comprises a liquid reservoir 35 with a chamber 32 containing the liquid substance to be injected in the patient's skin or other target tissue 34. In the second illustrative embodiment of FIG. 2, the liquid reservoir 35 is advantageously cylindrical to receive a spring-biased piston 36. More specifically, piston 36 is spring-biased toward the liquid chamber 32 by means of a helical spring 37 positioned in a gas-tight chamber 38. As illustrated in FIG. 2, the piston 36 is slidably mounted in the liquid reservoir 35 to divide this liquid reservoir 35 into the liquid chamber 32 and gas-tight chamber 38.

The liquid substance to be injected can be introduced in the liquid reservoir 32 through an inlet port 33. The inlet port 33 presents any suitable design allowing the liquid substance to be introduced in the liquid chamber 32 but preventing this liquid substance to escape from the liquid chamber 32 after it has been introduced in this liquid chamber 32. A first purging element 39 mounted on the liquid chamber 35 and a second purging element 40 mounted on the gas-tight chamber 38 can be opened whenever required. For example, opening of at least the purging element 40 during the supply of liquid substance in the liquid chamber 39 will allow gas to escape from the chamber 38 to thereby facilitate the introduction of the liquid substance in the liquid chamber 32. The quantity of liquid substance introduced in the liquid chamber 32 will depend, in particular but not exclusively, on the desired dosage.

The gas-tight chamber 38 is connected to an outlet $31_2$ of the reservoir 31 of pressurized gas through serially interconnected valve 41, intermediate chamber 42 and valve 42.

The needleless syringe 30 further comprises a convergent 44. Indeed, a convergent such as 44 can be used in the place of a convergent-divergent such as 17 of FIG. 1 when the required gas velocity is lower than the speed of the sound. However, it should be kept in mind that a convergent-divergent could be used in the place of the convergent in the second illustrative embodiment as illustrated in FIG. 2. As well, a convergent could be used in the place of the convergent-divergent in the first illustrative embodiment as illustrated in FIG. 1.

The upper end of the liquid chamber 32 communicates with the convergent 44 through a perforated membrane 45, for example a metallic or polymeric membrane 45 formed with at least one micro-orifice. The perforated membrane 45 can be similar to the above-described perforated membrane 22 of FIG. 1.

The end of larger diameter $44_1$ of the convergent 44 is connected to an outlet $31_1$ of the reservoir 31 of pressurized gas through serially interconnected valve 46, intermediate chamber 47 and valve 48.

The convergent 44 comprises an end of smaller diameter $44_2$ applied to or next to the skin or other target tissue 34 of the patient through a silencer and/or spacer 49. The function of the silencer 49 is to damp the sound produced by the flow of fluid. The function of the spacer is to ensure a desired stand-off distance between the end $44_2$ and the skin or other target tissue 34.

Again, the second illustrative embodiment of needleless syringe 30 generally comprises two systems:

- a first system for generating droplets (droplet generator) of given size at a pre-selected flow rate; and
- a second system for accelerating the droplets (droplet accelerator) at a pre-selected velocity and directing these droplets toward a predetermined location of the surface of the skin or other target tissue.

First System for Producing Droplets:

Referring to FIG. 2 of the appended drawings, the first system for generating droplets of given size at a pre-selected flow rate comprises:

- the reservoir of pressurized gas 31;
- the valve 41;
- the intermediate chamber 42;
- the valve 43;
- the liquid reservoir 35 including the gas-tight chamber 38, the spring-biased piston 36 and helical spring 37, and the liquid chamber 32; and
- the perforated membrane 45 and its at least one micro-orifice.

The valves 41 and 43 (FIG. 2) can be commercially available electronic valves suitable for this particular application and permitting an electronic control of the parameters of operation of the needleless syringe 30, in particular but not exclusively the gas pressure in the intermediate chamber 42 and 47, and the timing of the various operations.

Alternatively, FIGS. 3*a*, 3*b* and 3*c* illustrate valves 41 and 43 formed of pistons, plungers and springs. More specifically, as illustrated in FIGS. 3*a*, 3*b* and 3*c*:

- the valve 41 comprises a tubular member 50 interconnecting the intermediate chamber 42 with the outlet $31_2$ of the reservoir of pressurized gas 31, a L-shaped deviation line 51 of diameter smaller that the diameter of the tubular member 50 and extending between one side of the tubular member 50 and the secondary chamber 42, a plunger 52 slidably mounted in the tubular member 50 and normally obstructing the inlet $51_1$ from the tubular member 50 to the L-shaped deviation line 51, a piston 53 mounted at one end of the plunger 52, located in the intermediate chamber 42 and having a diameter larger than the diameter of the plunger 50, and a spring 54 mounted on the plunger 52 between the piston 53 and the inner surface of the intermediate chamber 42 around the tubular member 50; and the valve 43 comprises, inside the intermediate chamber 42, an axial hole 55 through the piston 53 and a section of the plunger 52, a piston 56 with an axial pin 57 slidably mounted in the axial hole 55, a spring 58 mounted one the axial pin 57 between the pistons 53 and 56, and a tubular member 59 between the secondary chamber 42 and the gas-tight chamber 38, the inlet $59_1$ from the intermediate chamber 42 to this tubular member 59 being normally closed by the piston 56.

Therefore, the pistons slide in each other but the amplitude of their respective strokes is limited by appropriately positioned stops.

Figure 2:
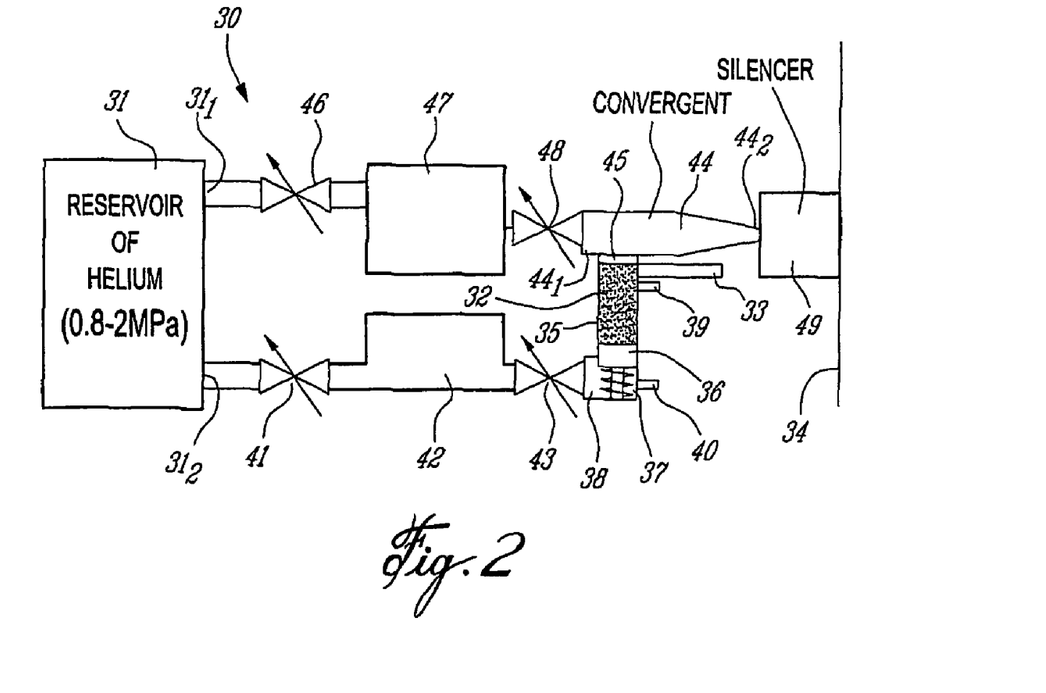
FIG. 2 is a schematic diagram illustrating the structure and operation of a second illustrative embodiment of needleless syringe in accordance with the present invention.

Second System for Accelerating the Droplets:

As a non-limitative example, the second system for accelerating the droplets comprises the valve 46, the intermediate chamber 47, the valve 48, the convergent 44, and the spacer/silencer 49.

Figure 3A:
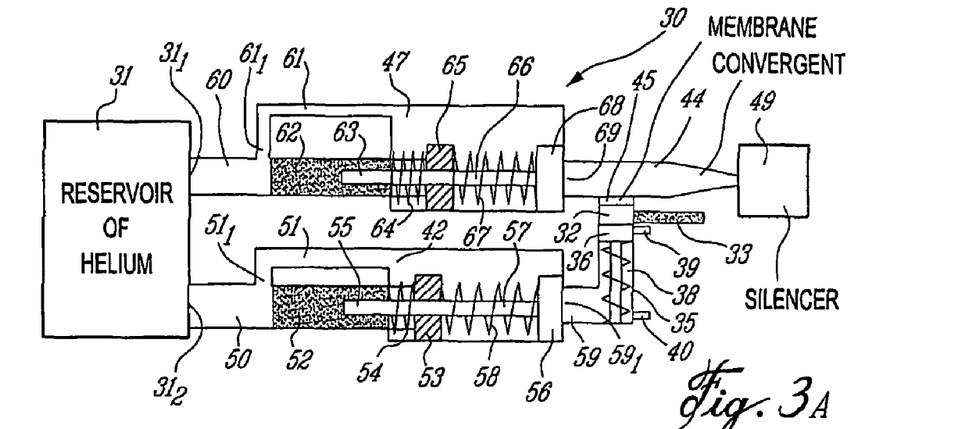
FIG. 3a is a first schematic diagram showing details of the structure and operation of the second illustrative embodiment of needleless syringe of FIG. 2.
Figure 3B:
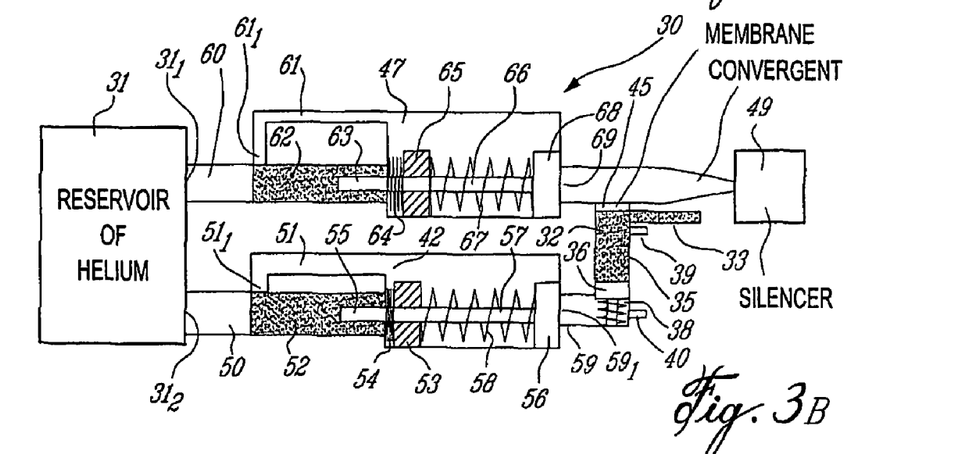
FIG. 3b is a second schematic diagram showing details of the structure and operation of the second illustrative embodiment of needleless syringe of FIG. 2.
Figure 3C:
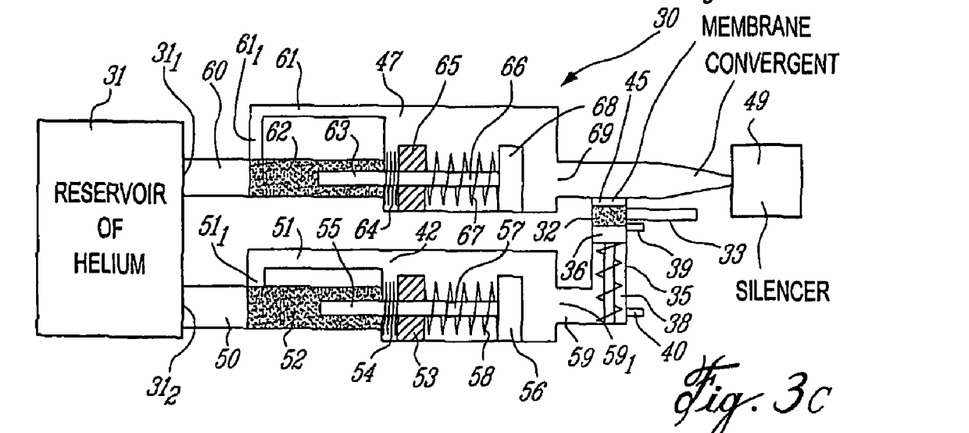
FIG. 3c is a third schematic diagram showing details of the structure and operation of the second illustrative embodiment of needleless syringe of FIG. 2.

The valves 46 and 48 (FIG. 2) can be commercially available electronic valves suitable for this particular application and permitting an electronic control of the parameters of operation of the needleless syringe, in particular but not exclusively the gas pressure in the secondary chamber 47, and the timing of the various operations.

Alternatively, FIGS. 3*a*, 3*b* and 3*c* illustrate valves 46 and 48 formed of pistons, plungers and springs. More specifically, as illustrated in FIGS. 3*a*, 3*b* and 3*c*:

the valve 46 comprises a tubular member 60 interconnecting the intermediate chamber 47 with the outlet $\mathbf{31}_1$ of the reservoir of pressurized gas 31, a L-shaped deviation line 61 having a diameter smaller than the diameter of the tubular member 60 and extending between one side of the tubular member 60 and the intermediate chamber 47, a plunger 62 slidably mounted in the tubular member 60 and normally obstructing the inlet $\mathbf{61}_1$ from the tubular member 50 to the L-shaped deviation line 61, a piston 65 mounted at one end of the plunger 62, located in the intermediate chamber 47 and having a diameter larger than the diameter of the plunger 62, and a helical spring 64 mounted on the plunger 62 between the piston 65 and the inner surface of the intermediate chamber 47 around the tubular member 60; and the valve 48 comprises, inside the intermediate chamber 47, an axial hole 63 through the piston 65 and a section of the plunger 62, a piston 68 with an axial pin 66 slidably mounted in the axial hole 63, a helical spring 67 mounted on the axial pin 66 between the pistons 65 and 68, and an outlet 69 of the intermediate chamber 47 to the convergent 44 normally closed by the piston 68.

Therefore, the pistons slide in each other but the amplitude of their respective strokes is limited by appropriately positioned stops.

Operation of the Second Illustrative Embodiment of Needleless Syringe

An example of operation of the second illustrative embodiment of the needleless syringe 30 of FIG. 2 will now be described with reference to FIGS. 3*a*, 3*b* and 3*c*.

Pistons 53 and 65 are initially in the respective positions shown in FIG. 3*a*. In these positions of the pistons 53 and 65, the plunger 52 opens the inlet $\mathbf{51}_1$ of the deviation line 51 to allow pressurized gas from the reservoir 31 to flow toward the intermediate chamber 42 through the outlet $\mathbf{31}_2$, the tubular member 50, and the deviation line 51. In the same manner, the plunger 62 opens the inlet $\mathbf{61}_1$ of the deviation line 61 to allow pressurized gas from the reservoir 31 to flow toward the intermediate chamber 47 through the outlet $\mathbf{31}_1$, the tubular member 60, and the deviation line 61.

After the intermediate chambers 42 and 47 are full of pressurized gas from the reservoir 31, the pistons 53 and 65 are moved to the respective positions shown in FIG. 3*b* against the force produced by the springs 54 and 64, respectively. The plunger 52 then seals the inlet $\mathbf{51}_1$ while the plunger 62 seals the inlet $\mathbf{61}_1$.

A liquid substance is then introduced in the liquid chamber 32 through, for example, the inlet port 33. The purging elements 39 and 40 can be used during this operation to provide for escape of air from the chambers 32 and 38 and thereby facilitate downward movement of the piston 36 and thereby introduction of the liquid substance within the liquid chamber 32. The purging elements 39 and 40 are then sealed.

The pistons 56 and 68 are then displaced toward the pistons 53 and 65, respectively, against the force produced by the springs 58 and 67, respectively (see FIG. 3*c*). Displacement of the piston 56 toward the piston 53 causes sliding of the axial pin 57 in the axial hole 55 and opening of the inlet $\mathbf{59}_1$ to the tubular member 59 and gas-tight chamber 38. In the same manner, displacement of the piston 68 toward the piston 65 causes sliding of the axial pin 66 in the axial hole 63 and opening of the inlet 69 to the convergent 44.

Opening of the inlet 69 causes release of the pressurized gas from the intermediate chamber 47 to the convergent 44 to produce in the convergent 44 and silencer 49 the high velocity jet of inert gas (FIG. 3*c*).

Opening of the inlet $\mathbf{59}_1$ causes the pressurized gas from the intermediate chamber 38 to flow toward the gas-tight chamber 38 of the liquid reservoir 35 through the tubular member 59 to apply a corresponding pressure on the piston 36 and thereby force liquid substance from the liquid chamber 32 to flow through the micro-orifices such as 23 (FIG. 4) to produce the jet of liquid substance 24 (FIG. 4) on the side of the membrane 45 opposite to the liquid chamber 32. This jet 24 is transformed into droplets 25 (FIGS. 3*c* and 4) of liquid substance through natural flow instabilities which are caught and conveyed by the high velocity jet of gas 70 through the convergent 44 and the silencer 49 for finally being injected in the skin or other target tissue 34 (FIG. 2) of the patient.

Although this is not required for the needleless syringe to operate, the valve 48 (piston 68) is advantageously opened before the valve 43 (piston 56) is opened to enable the establishment of a steady-state high velocity jet of gas through the convergent 44 before the droplets 25 are produced and introduced into this high velocity jet of gas. This ensures a uniform velocity of the droplets 25.

The needleless syringe according to the first and second illustrative embodiments may further comprise the following non-limitative variants:

if a convergent-divergent such as 17 (FIG. 1) is used, the diameter of the outlet $\mathbf{31}_1$ of the reservoir of pressurized gas 31 has a diameter equal to or larger than the diameter of the collar section 19 of this convergent-divergent 17;

a triggering system (not shown), for example an electronic circuit or a mechanism, for operating the valves of the needleless syringe according to the first and second illustrative embodiments is provided for; this triggering system can be a mechanism for operating the pistons 53, 56, 65 and 68 as described hereinabove with reference to FIGS. 3*a*, 3*b* and 3*c*;

the reservoir 31 of pressurized gas can be under the form of a replaceable or refillable unit;

the needleless syringe is a disposable syringe;

the pressure of gas in the intermediate chambers 42 and 47 can be adjusted by means of, for example, spring-biased mechanical mano-relief valves since, to obtain a uniform velocity of the droplets during the first as well as during the last injection, the gas pressure in the intermediate chambers 42 and 47 must be the uniform from one injection to the other to thereby ensure repeatability of the parameters of injection at each use of the needleless syringe;

the gas pressure in the reservoir 31 is sufficiently high to allow the needleless syringe to perform a given number of injections;

the membrane 22, 45 is a replaceable unit, and the number of micro-orifices such as 25 can be adapted to the flow rate of liquid substances required by the intended application;

the liquid substance can be introduced in the liquid chamber 32 by means of a depression produced in the air-tight chamber 38 and, when the piston 36 has reached its lower position, it is blocked until the syringe is triggered;

many alternatives for introducing the liquid substance to be injected in the liquid reservoir can be envisaged; examples are syringes with needles, pre-loaded capsules especially designed for the intended application, or a capsule that can be used for many injections (for example for diabetes); and as indicated in the foregoing description, instead of valves formed of pistons, plungers and springs as illustrated in FIGS. 3*a*, 3*b* and 3*c*, the valves 16 and 21 (FIG. 1), and the valves 41, 43, 46 and 48 (FIG. 2) can be commercially available electronic valves suitable for this particular application and permitting an electronic control of the parameters of operation of the needleless syringe, in particular but not exclusively the gas pressure in the intermediate chambers such as 42 and 47, and the timing of the various operations.

Third Illustrative Embodiment of the Needleless Syringe

Figure 5:
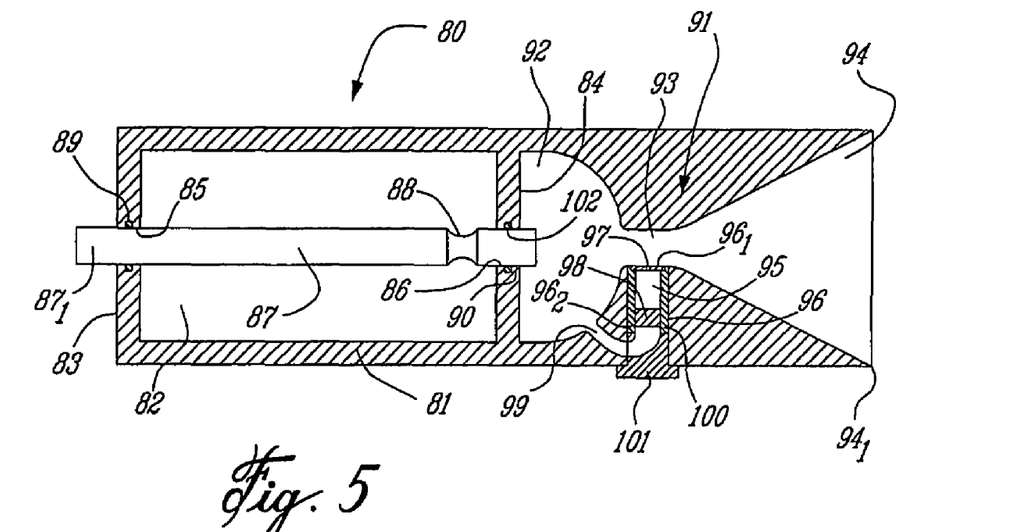
FIG. 5 is a schematic diagram illustrating the structure of a third illustrative embodiment of needleless syringe in accordance with the present invention.

Referring to FIG. 5, the third illustrative embodiment of needleless syringe 80 comprises a body 81 made, for example, of molded plastic material. The body 81 defines an axial reservoir 82 containing pressurized gas, for example a high pressure inert gas such as helium at a pressure of 0.8 to 2 MPa.

The reservoir 82 defines an end transversal wall 83 and an inner transversal wall 84. Transversal wall 83 comprises a central, axial hole 85 while transversal wall 84 comprises a central, axial hole 86. An elongated rod 87 extends through both the holes 85 and 86, this elongated rod 87 comprising an annular notch 88 inside the reservoir 82 in the proximity of the hole 86. To prevent leakage of pressurized gas from the reservoir 82, a first O-ring 89 is mounted between the hole 85 and the outer surface of the rod 87 while a second O-ring 102 is mounted between the hole 86 and the outer surface of the rod 87.

The body 81 of the needleless syringe 80 further comprises a convergent-divergent 91 on the side of the wall 84 opposite to the reservoir 82. The convergent-divergent 91 comprises, in series from the wall 84, a convergent 92, throat 93 and a divergent 94.

The third illustrative embodiment of needleless syringe 80 further comprises a reservoir of liquid 95 containing the liquid substance to be injected in the patient's skin or other target tissue (not shown in FIG. 5). The quantity of liquid substance will depend, in particular but not exclusively, on the required dosage. In the third illustrative embodiment, the reservoir of liquid 95 is under the form of a cylinder 96 embedded in the material of the body 81, and having a first end 96$_1$ communicating with the throat 93 through a perforated membrane 97, for example a metallic or polymeric membrane formed with at least one micro-orifice. In the third illustrative embodiment of FIG. 5, the cylinder 96 also comprises a second end 96$_2$ closed by means of a piston 98. The end 96$_2$ of the cylinder 96 communicates with the upstream end of the inside of the convergent 92 through a deviation line 99 formed in the body 81 of the third preferred embodiment of needleless syringe 80.

The third illustrative embodiment of needleless syringe 80 generally comprises two systems:

a first system for generating droplets (generator of droplets) of given small size at a pre-selected flow rate; and a second system for accelerating the droplets (droplet accelerator) at a pre-selected speed while directing these droplets toward a predetermined location of the surface of the skin or other target tissue.

First System for Generating Droplets:

Referring to FIG. 5 of the appended drawings, the first system for generating droplets of given size at a pre-selected flow rate comprises:

the reservoir of pressurized gas;

the valve formed by the holes 85 and 86, the rod 87 with the annular notch 88, and the O-rings 89 and 90;

the divergent 92 and deviation line 99; and the reservoir of liquid 95 comprising the cylinder 96, the perforated membrane 97 and the piston 98.

Second System for Accelerating the Droplets:

As a non-limitative example, the second system for accelerating the droplets (droplet accelerator) comprises the:

the reservoir of pressurized gas 82;

the valve formed by the holes 85 and 86, the rod 87 with the annular notch 88, and the O-rings 89 and 90; and the convergent-divergent 91.

Operation of the Third Illustrative Embodiment of Needleless Syringe

Figure 4:
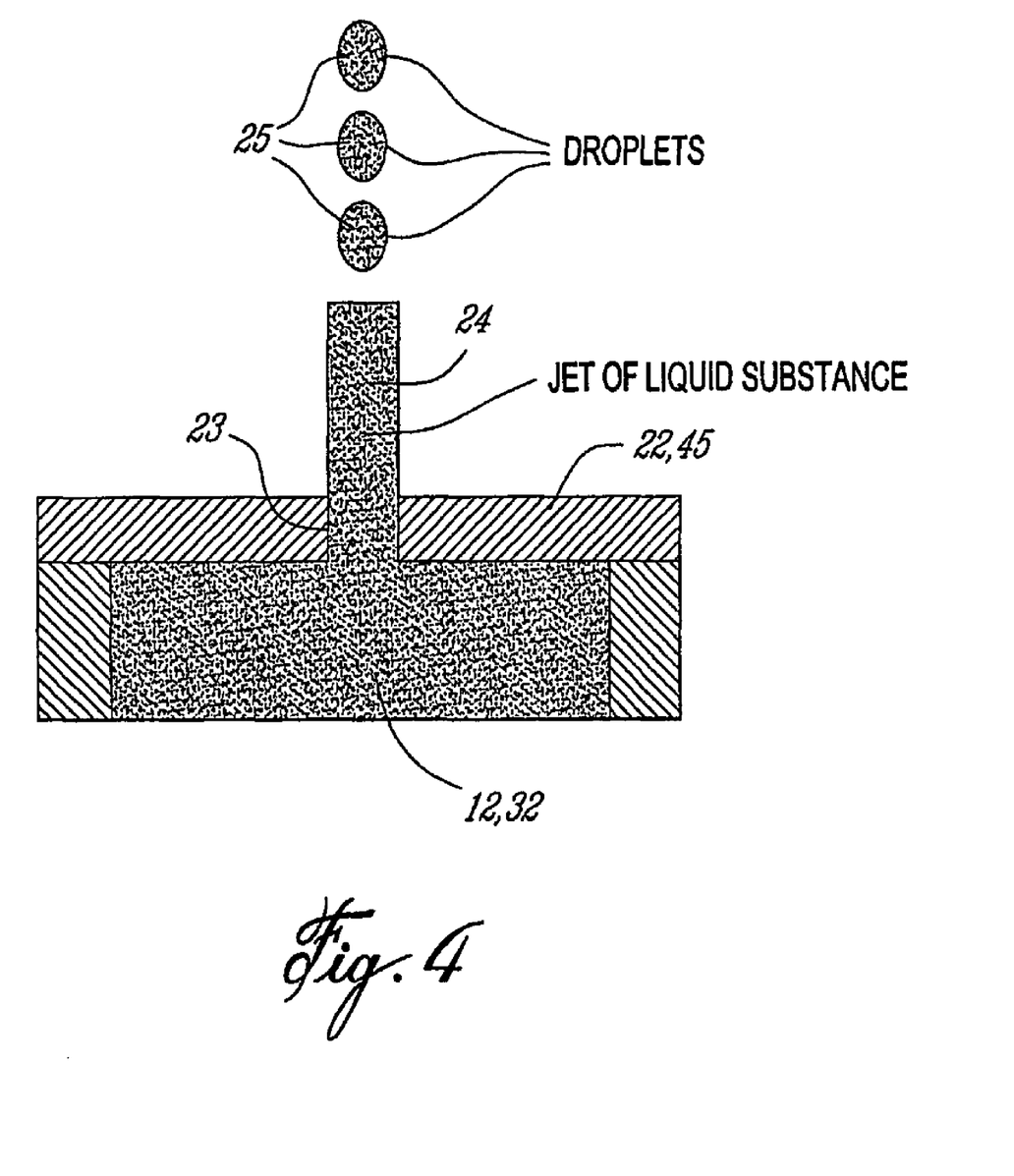
FIG. 4 is a schematic diagram illustrating a process of production of droplets as used in the first and second illustrative embodiments of needleless syringe as shown in FIGS. 1 and 2.

The third illustrative embodiment of needleless syringe 80 of FIG. 5 operates as follows:

the outer, free end 87$_1$ of the rod 87 is pushed toward the wall 83 to enable supply of pressurized gas from the reservoir 82 to the convergent 92 through the gap between the notch 88 and the hole 86 and thereby establish a high velocity jet of gas through the convergent 92, throat 93 and divergent 94 of the convergent-divergent 91;

the pressurized gas supplied to the convergent 92 also apply a pressure to the piston 98 through the deviation line 99 to thereby force liquid substance from the reservoir 82 through the above described at least one micro-orifice of the perforated membrane 97;

as described with reference to FIG. 4, passage of liquid substance though each micro-orifice such as 23 of the perforated membrane 97 produces, on the side of the membrane 97 opposite to the reservoir 95, a jet such as 24 of liquid substance, this jet being transformed into droplets such as 25; and the droplets are accelerated by the high velocity jet of gas established through the convergent-divergent 91, in particular through the throat 93, toward the patient's skin or other target tissue (not shown in FIG. 5).

In the third illustrative embodiment of FIG. 5:

a plug of any design can be used to cover and protect the perforated membrane 97 during storage;

any other type of valve can be used to isolate the pressurized gas reservoir from the convergent, for example a double burstable membrane as will be described in the following description;

a silencer (not shown) can be mounted on the free end $94_1$ of the divergent 94 to reduce noise;

a spacer (not shown) can be mounted on the free end $94_1$ of the divergent 94 to ensure a preset stand-off distance from the target tissue; and/or the liquid reservoir 95, including the cylinder 96, the perforated membrane 97 and the piston 98 can be designed as a separate unit that can be inserted in an appropriately shaped cavity 100 of the body 81 through a side opening 101. The side opening 101 can then be sealed either permanently for example by a press-fit plug 102 or non-permanently for example through a screwed plug.

Fourth Illustrative Embodiment of the Needleless Syringe

Figure 6:
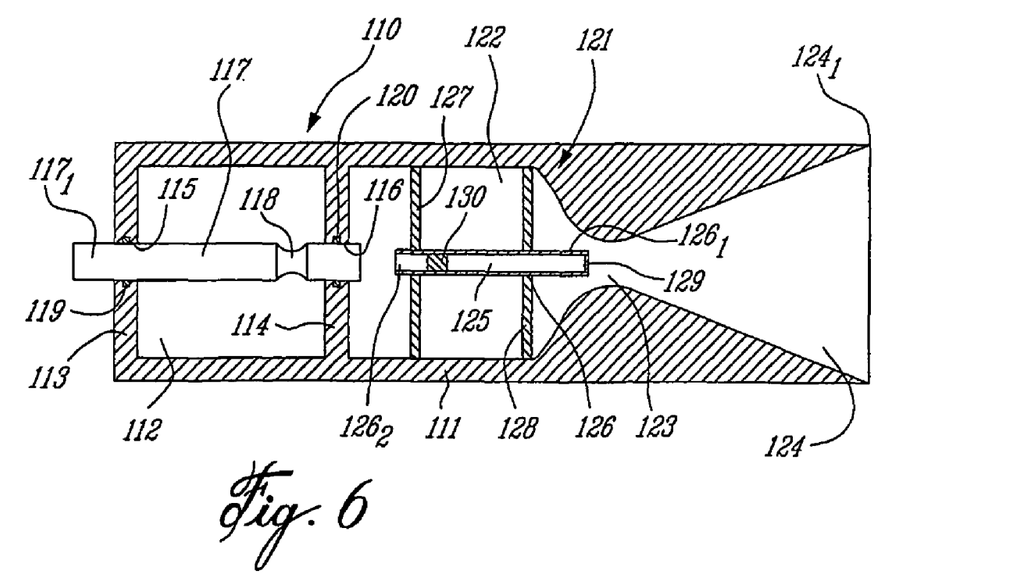
FIG. 6 is a schematic diagram illustrating the structure of a fourth illustrative embodiment of needleless syringe in accordance with the present invention.

Referring to FIG. 6, the fourth illustrative embodiment of needleless syringe 110 also comprises a body 111 made, for example, of molded plastic material. The body 111 defines an axial reservoir 112 containing pressurized gas, for example a high pressure inert gas such as helium at a pressure of 0.8 to 2 MPa.

The reservoir 112 defines an end transversal wall 113 and an inner transversal wall 114. Transversal wall 113 comprises a central, axial hole 115 while transversal wall 114 comprises a central, axial hole 116. An elongated rod 117 extends through both the holes 115 and 116, this elongated rod 117 comprising an annular notch 118 inside the reservoir 112 in the proximity of the hole 116. To prevent leakage of pressurized gas from the reservoir 112, a first O-ring 119 is mounted between the hole 115 and the outer surface of the rod 117 while a second O-ring 120 is mounted between the hole 116 and the outer surface of the rod 117.

The body 111 of the needleless syringe 110 further comprises a convergent-divergent 121 on the side of the wall 114 opposite to the reservoir 112. The convergent-divergent 121 comprises, in series from the wall 114, a convergent 122, throat 123 and a divergent 124.

The fourth illustrative embodiment of needleless syringe 110 further comprises a reservoir of liquid 125 containing the liquid substance to be injected in the patient's skin or other target tissue (not shown in FIG. 6). The quantity of liquid substance will depend, in particular but not exclusively, on the required dosage. In the fourth illustrative embodiment, the reservoir of liquid 115 is under the form of a cylinder 126 mounted axially in the convergent 122 through axially spaced apart support members 127 and 128 extending between the outer surface of the cylinder 126 and the inner surface of the convergent 122 but structured not to impede the flow of high velocity jet of gas. The cylinder 126 has a distal end $126_1$ communicating with the throat 123 through a perforated membrane 129, for example a metallic or polymeric membrane formed with at least one micro-orifice. In the fourth illustrative embodiment of FIG. 6, the cylinder 126 also comprises a second end $126_2$ located in the proximity of the hole 116 in the wall 114 and closed by means of a piston 130.

The fourth illustrative embodiment of needleless syringe 80 generally comprises two systems:

a first system for generating droplets (generator of droplets) of given small size at a pre-selected flow rate; and a second system for accelerating the droplets (droplet accelerator) at a pre-selected speed while directing these droplets toward a predetermined location of the surface of the skin or other target tissue.

First System for Generating Droplets:

Referring to FIG. 6 of the appended drawings, the first system for generating droplets of given size at a pre-selected flow rate comprises:

the reservoir of pressurized gas 112;

the valve formed by the holes 115 and 116, the rod 117 with the annular notch 118, and the O-rings 119 and 120;

the convergent 122; and the reservoir of liquid 125 comprising the cylinder 126, the perforated membrane 129 and the piston 130.

Second System for Accelerating the Droplets:

As a non-limitative example, the second system for accelerating the droplets (droplet accelerator) comprises the:

the reservoir of pressurized gas 112;

the valve formed by the holes 115 and 116, the rod 117 with the annular notch 118, and the O-rings 119 and 120; and the convergent-divergent 121.

Operation of the Fourth Illustrative Embodiment of Needleless Syringe

The fourth illustrative embodiment of needleless syringe 110 of FIG. 6 operates as follows:

the outer, free end $117_1$ of the rod 117 is pushed toward the wall 113 to enable supply of pressurized gas from the reservoir 112 to the convergent 122 through the space between the annular notch 118 and the hole 116, and thereby establish a high velocity jet of gas through the convergent 122, throat 123 and divergent 124 of the convergent-divergent 121;

the pressurized gas supplied to the convergent 122 also apply a pressure to the piston 130 to thereby force liquid substance from the reservoir 125 through the above described at least one micro-orifice of the perforated membrane 129;

as described with reference to FIG. 4, passage of liquid substance though each micro-orifice such as 23 of the perforated membrane 129 produces, on the side of the membrane 129 opposite to the reservoir 125, a jet such as 24 of liquid substance, this jet being transformed into droplets such as 25; and the droplets are accelerated by the high velocity jet of gas established through the convergent-divergent 121, in particular through the throat 123, toward the patient's skin or other target tissue (not shown in FIG. 6).

In the fourth illustrative embodiment of FIG. 6:

a cap of any design can be used to cover and protect the perforated membrane 129 during storage;

any other type of valve can be used to isolate the pressurized gas reservoir from the convergent, for example a double burstable membrane as will be described in the following description;

a silencer (not shown) can be mounted on the free end $124_1$ of the divergent 124 to reduce noise;

a spacer (not shown) can be mounted on the free end $124_1$ of the divergent 124 to ensure a preset stand-off distance from the target tissue; and/or the liquid reservoir 125, including the cylinder 126, the perforated membrane 129 and the piston 130 can be designed as a separate unit that can be inserted on appropriately designed support members 127 and 128 through the end 124₁ of the divergent 124, or by separating the body 121 in the convergent region 122.

Fifth Illustrative Embodiment of the Needleless Syringe

Figure 7:
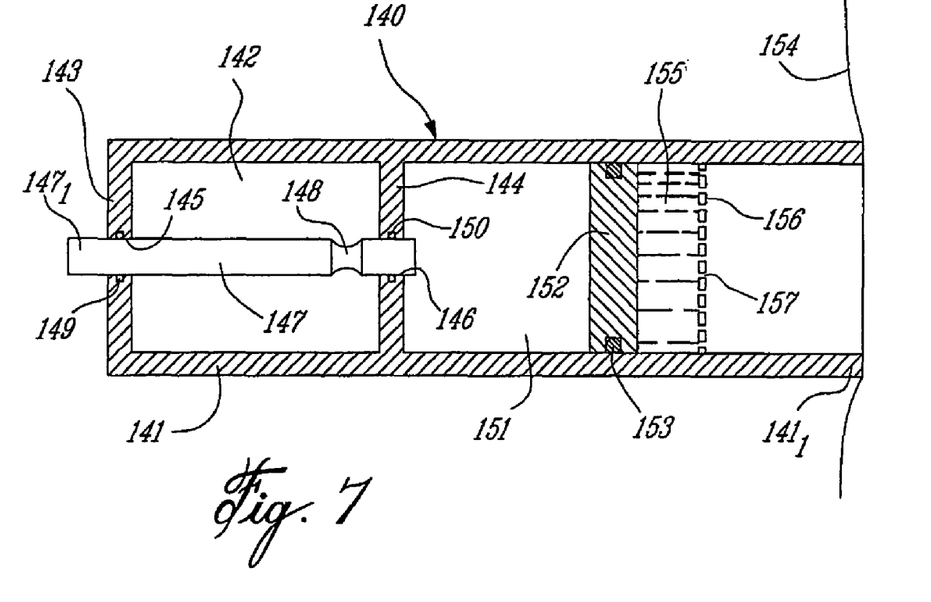
FIG. 7 is a schematic diagram illustrating the structure of a fifth illustrative embodiment of needleless syringe in accordance with the present invention.

Referring to FIG. 7, the fifth illustrative embodiment of needleless syringe 140 comprises a cylindrical body 141 made, for example, of molded plastic material. The body 141 defines an axial reservoir 142 containing pressurized gas, for example a high pressure inert gas such as helium at a pressure of 0.8 to 2 MPa.

The reservoir 142 defines an end transversal wall 143 and an inner transversal wall 144. Transversal wall 143 comprises a central, axial hole 145 while transversal wall 144 comprises a central, axial hole 146. An elongated rod 147 extends through both the holes 145 and 146, this elongated rod 147 comprising an annular notch 148 inside the reservoir 142 in the proximity of the hole 146. To prevent leakage of pressurized gas from the reservoir 142, a first O-ring 149 is mounted between the hole 145 and the outer surface of the rod 147 while a second O-ring 150 mounted between the hole 146 and the outer surface of the rod 147.

The body 141 of the needleless syringe 140 further defines, on the side of the wall 144 opposite to the reservoir 142 and from this wall 144 to the end 141₁ of the cylindrical body 141, a series arrangement including a chamber 151 containing gas at low pressure, for example 1 atmosphere, a piston 152 with an annular seal such as an O-ring 153 between the peripheral edge surface of the piston 152 and the inner surface of the cylindrical body 141, a chamber 155 containing liquid substance to be injected in the patient's skin or other target tissue 154, and a perforated membrane 156, for example a metallic or polymeric membrane formed with micro-orifices such as 157. Again, the quantity of liquid substance will depend, in particular but not exclusively, on the required dosage.

Operation of the Fifth Illustrative Embodiment of Needleless Syringe

The fifth illustrative embodiment of needleless syringe 140 of FIG. 7 operates as follows:
- the outer, free end 147₁ of the rod 147 is pushed toward the wall 143 to enable supply of pressurized gas from the reservoir 142 to the chamber 151 through the gap between the notch 148 and the hole 146;
- the pressurized gas supplied to the chamber 151 will apply a pressure to the piston 152 to thereby force liquid substance from the chamber 155 through the above described micro-orifices of the perforated membrane 157;
- as described with reference to FIG. 4, passage of liquid substance though each micro-orifice such as 156 of the perforated membrane 156 produces, on the side of the membrane 156 opposite to the chamber 155, a jet such as 24 of liquid substance, this jet being transformed into droplets such as 25; and
- the pressure of the gas supplied in the chamber 151 is sufficiently high to project and direct the droplets of liquid substance toward the patient's skin or other target tissue with a velocity sufficient to inject these droplets of liquid substance in the patient's skin or other target tissue.

In the fifth illustrative embodiment of FIG. 7:
- a plug or cap of any design can be used to cover and protect the perforated membrane 156 during storage;
- the piston 152 can be a thin flexible membrane deformed by the gas under pressure;
- a silencer (not shown) can be mounted on the free end 141₁ of the cylindrical body 141 to reduce noise;
- the above described gas driving system to apply pressure to the piston 152 or flexible membrane can be replaced by any suitable spring driver system or chemical propellant driving system; and/or
- the perforated membrane 156 is located at a pre-determined stand-off distance from the patient's skin, or other target tissue 154, according to each particular application.

Sixth Illustrative Embodiment of the Needleless Syringe

Figure 8:
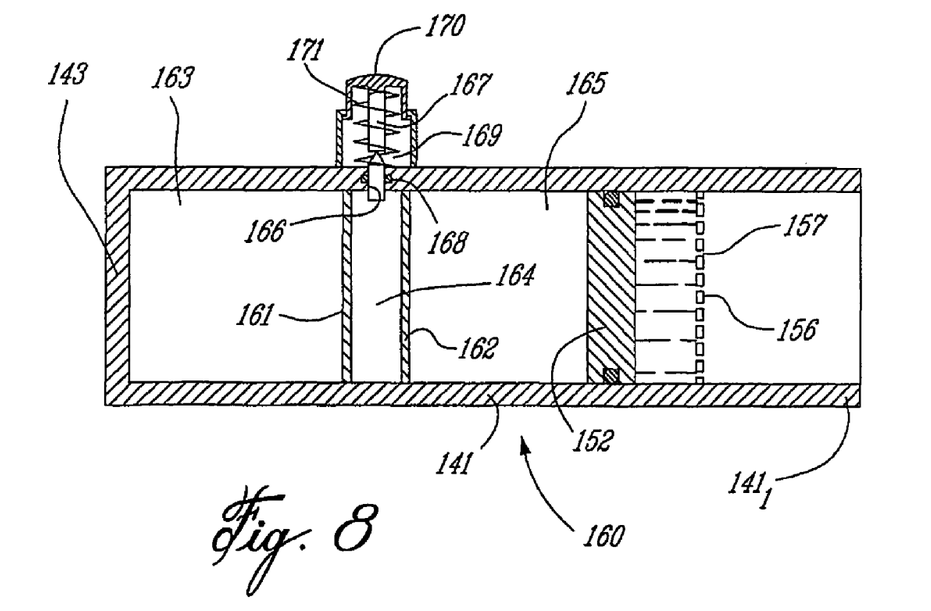
FIG. 8 is a schematic diagram illustrating the structure of a sixth illustrative embodiment of needleless syringe in accordance with the present invention.

Referring to FIG. 8, the sixth illustrative embodiment of needleless syringe 160 is similar to the fifth illustrative embodiment of FIG. 7, except that the valve system of FIG. 7 including the wall 144, the axial holes 145 and 146, the elongated rod 147 and the O-rings 149 and 150 is replaced by a pair of transversal, burstable membranes 161 and 162.

As illustrated in FIG. 8, the reservoir of pressurized gas 163 is defined in the cylindrical body between the end wall 143 and the membrane 161, a first gas-containing chamber 164 is defined between the membranes 161 and 162, and a second gas-containing chamber 165 is defined between the membrane 162 and the piston 152. In this sixth illustrative embodiment, the membranes 161 and 162 are capable of withstanding a pressure of ½ $p_2$ or higher. As the pressure of the gas in the reservoir 163 is $p_2$, the pressure of the gas in the chamber 164 is about ½ $p_2$, and the pressure of the gas in the chamber 165 is 1 atmosphere, the membranes 161 and 162 are capable of withstanding the pressure differentials.

A hole 166 is made through the wall of the cylindrical body 141, this hole 166 opening into the chamber 164. A spring-biased plunger 167 is inserted in the hole 166 with a seal such as an O-ring 168 positioned between the plunger 167 and the hole 166 to prevent escape of gas from the chamber 164. On the outside of the cylindrical body 141, the plunger 167 is formed with an annular notch 169, and is provided with a head 170 and a spring 171 interposed between the head 170 and the outer surface of the cylindrical body 141.

Momentary depression of the spring-biased plunger 167 will allow gas from the chamber 164 to escape through the gap between the annular notch 169 and the hole 166 to thereby increase the differential of pressure between the opposite sides of the membrane 161. The pressure of the gas in the reservoir 163 will then burst the membrane 161 to supply the chamber 164 with pressurized gas which, in turn, will burst the membrane 162. Of course, the resistance of the membranes 161 and 162 are designed to burst in response to momentary depression of the plunger 167, and the plunger allows a minimal amount of gas to escape from the hole 166 but just sufficient to enable the burst of the membranes 161 and 162.

The pressurized gas from the reservoir will then apply pressure to the piston 152 with the same result as described with reference to the fifth embodiment of FIG. 7.

In the sixth illustrative embodiment of FIG. 8:
- a cap or plug of any design can be used to cover and protect the perforated membrane 156 during storage;
- a silencer (not shown) can be mounted on the free end 141₁ of the cylindrical body 141;
- any other valve mechanism can be used to replace the hole 166, the spring-biased plunger 167, and the seal 168 in order to momentarily vent the gas from the chamber 164 such that membrane 161 is caused to burst with minimal gas from reservoir 163 escaping to the atmosphere outside the needleless syringe 160;

the perforated membrane can be replaced by a lattice or trellis; and/or if in sufficiently small quantity, the liquid substance can be placed on the downstream side of the perforated membrane, lattice or trellis where it could be retained by surface tension; in this case the piston 152 would not be required.

Seventh Illustrative Embodiment of the Needleless Syringe

Figure 9A:
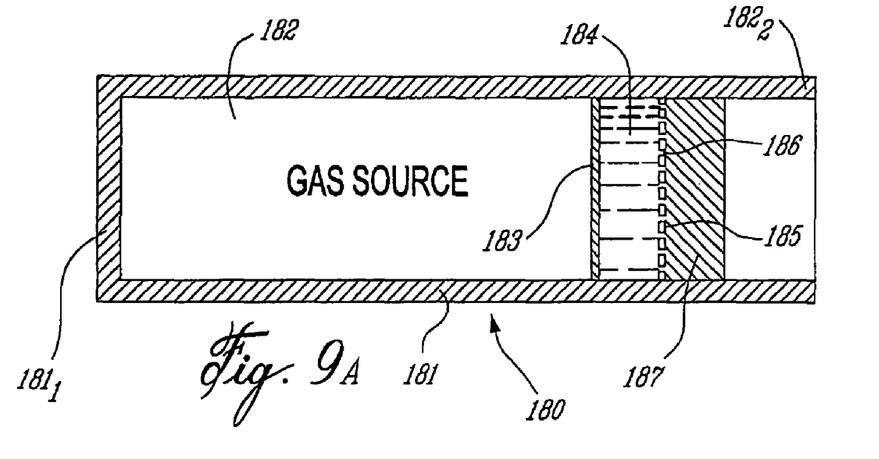
FIG. 9a is a first schematic diagram illustrating the structure and operation of a seventh illustrative embodiment of needleless syringe in accordance with the present invention.
Figure 9B:
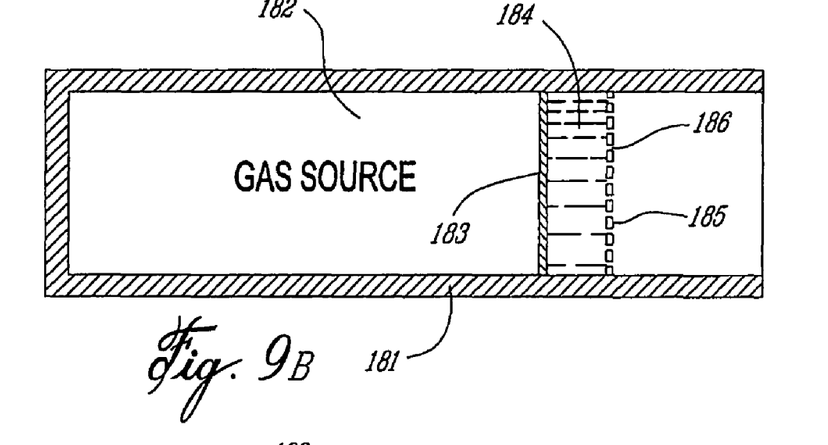
FIG. 9b is a second schematic diagram illustrating the structure and operation of the seventh illustrative embodiment of needleless syringe in accordance with the present invention.
Figure 9C:
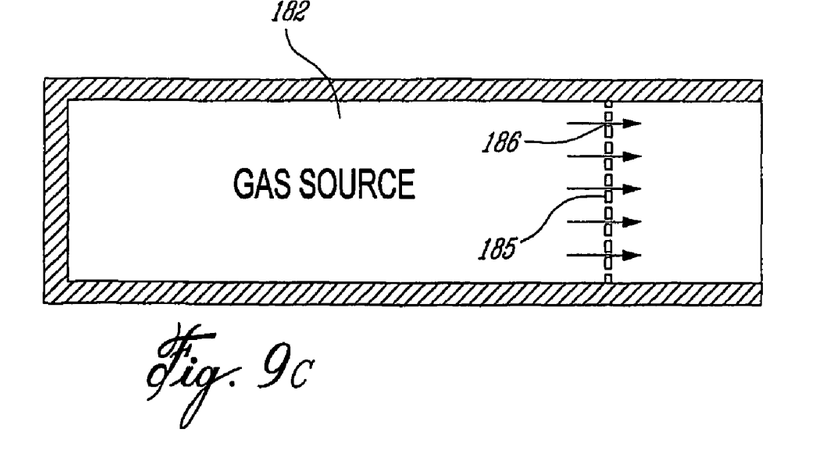
FIG. 9c is a third schematic diagram illustrating the structure and operation of the seventh illustrative embodiment of needleless syringe in accordance with the present invention.

Referring to FIGS. 9a, 9b and 9c, the seventh illustrative embodiment of needleless syringe 180 comprises a cylindrical body 181 made, for example, of molded plastic material.

The body 181 contains, from a closed end $181_1$ to an open end $181_2$ thereof, a gas source 182, a burstable membrane 183, a chamber 184 containing liquid substance to be injected in the patient's skin or other target tissue, a perforated membrane 185 with at least one micro-orifice 186, and a cap 187 for covering and protecting the perforated membrane 185.

For example, the gas source 182 can be formed either by:

the reservoir 142, wall 143, wall 144, hole 145, hole 146, rod 147, O-ring 149, O-ring 150 and chamber 151 of FIG. 7; or the burstable membranes 161 and 162, the reservoir of pressurized gas 163, the first gas-containing chamber 164, the second gas-containing chamber 165, and the spring-biased plunger 167 of FIG. 8.

Operation of the Seventh Illustrative Embodiment of Needleless Syringe

The seventh illustrative embodiment of needleless syringe 140 of FIGS. 9a, 9b and 9c operates as follows:

the cap 187 is removed (FIG. 9b);

pressurized gas from the gas source 182 is released as described, for example, either with reference to FIG. 7 or 8 to apply a pressure to the burstable membrane 183;

the resistance of the membrane 183 is so selected that the released pressurized gas will burst this membrane 183 (FIG. 9b); and after bursting of the membrane 183, the pressurized gas forces liquid substance through the micro-orifices 186 of the membrane 185 to produce both high velocity jets of gas and droplets accelerated to a sufficiently high velocity for being injected in the patient's skin or other target tissue.

In a general, non-limitative manner, the size of the droplets such as 25 (FIG. 4) will normally vary within the range of 1 to 1000 microns and the velocity of the jet of gas within the range of 10 to 1000 m/s, depending on the specific application. Of course, the present invention is intended to cover sizes and velocities located outside of these ranges.

Although the present invention has been described hereinabove with reference to illustrative embodiments thereof, it should be kept in mind that these illustrative embodiments can be modified at will, within the scope of the appended claims, without departing from the spirit and nature of the subject invention. For instance, the present invention is intended to cover a needleless syringe comprising any combination of any features as described in the foregoing specification.

What is claimed is:

1. A method for needleless injection of a liquid substance into a target biological tissue, comprising:
    generating a high velocity jet of gas;
    generating droplets of the liquid substance;
    supplying and conveying the droplets of the liquid substance into the high velocity jet of gas; and
    guiding the high velocity jet of gas through a channel toward a surface of the target biological tissue for injecting the conveyed droplets of the liquid substance into the target biological tissue;
    wherein generating the droplets of the liquid substance comprises:
        containing the liquid substance into a reservoir;
        interposing a perforated membrane between the reservoir and the channel in such a manner that the flow of the high velocity jet of gas is guided along a face of the perforated membrane on a side of the perforated membrane opposite to the reservoir of the liquid substance; and
        pressurizing the reservoir containing the liquid substance to force the liquid substance from the liquid reservoir through the perforated membrane to thereby produce a jet of the liquid substance that transforms into a stream of the droplets supplied within the high velocity jet of gas laterally of the direction of the flow said high velocity jet of gas.

2. A method for needleless injection of a liquid substance as defined in claim 1, wherein generating the high velocity jet of gas comprises:
    supplying pressurized gas from a gas reservoir to a convergent-divergent.

3. A method for needleless injection of a liquid substance as defined in claim 1, wherein generating the high velocity jet of gas comprises:
    supplying pressurized gas from a gas reservoir to a convergent.

4. A method for needleless injection of a liquid substance as defined in claim 1, wherein generating the high velocity jet of gas comprises generating a jet of inert gas.

5. A method for needleless injection of a liquid substance as defined in claim 1, wherein generating the droplets of the liquid substance comprises forcing the liquid substance from the liquid reservoir through at least one micro-orifice of the perforated membrane.

6. A method for needleless injection of a liquid substance as defined in claim 1, wherein pressurizing the reservoir containing the liquid substance comprises:
    supplying pressurized gas from a gas reservoir to the reservoir containing the liquid substance.

7. A method for needleless injection of a liquid substance as defined in claim 1, comprising generating the high velocity jet of gas prior to generating the droplets of the liquid substance to thereby supply the droplets of the liquid substance in a steady-state high velocity jet of gas.

8. A needleless syringe for injecting a liquid substance into a target biological tissue, comprising:
    a generator of high velocity jet of gas;
    a generator of droplets of the liquid substance having an outlet for supplying the droplets of the liquid substance into the high velocity jet of gas whereby the droplets of the liquid substance are conveyed within the high velocity jet of gas; and
    a channel for guiding the high velocity jet of gas toward a surface of the target biological tissue to thereby inject the conveyed droplets of the liquid substance into the target biological tissue;

wherein the generator of the droplets of the liquid substance comprises:

a reservoir containing the liquid substance;

a perforated membrane interposed between the reservoir of the liquid substance and the channel for guiding the high velocity jet of gas; and a source of pressurization of the reservoir containing the liquid substance to force the liquid substance from the liquid reservoir through the perforated membrane to thereby produce a jet of the liquid substance that transforms into a stream of the droplets; and wherein the perforated membrane is interposed between the liquid reservoir and the channel for guiding the flow of the high velocity jet of gas along a face of the perforated membrane on a side of the perforated membrane opposite to the liquid reservoir, whereby the jet of the liquid substance and the generated droplets of the liquid substance are supplied within the high velocity jet of gas laterally of the direction of the flow of said high velocity jet of gas.

9. A needleless syringe for injecting a liquid substance as defined in claim 8, wherein the generator of high velocity jet of gas comprises:

a convergent-divergent having an inlet; and a pressurized gas supply connected to the inlet of the convergent-divergent to supply pressurized gas to the convergent-divergent and thereby generate the high velocity jet of gas.

10. A needleless syringe for injecting a liquid substance as defined in claim 9, wherein the pressurized gas supply comprises:

a reservoir of pressurized gas; and a valve interposed between the reservoir of pressurized gas and the inlet of the convergent-divergent to controllably supply pressurized gas from the reservoir of pressurized gas to the inlet of the convergent-divergent and thereby generate the high velocity jet of gas.

11. A needleless syringe for injecting a liquid substance as defined in claim 8, wherein the generator of high velocity jet of gas comprises:

a convergent having an inlet; and a pressurized gas supply connected to the inlet of the convergent to supply pressurized gas to the convergent and thereby generate the high velocity jet of gas.

12. A needleless syringe for injecting a liquid substance as defined in claim 11, wherein the pressurized gas supply comprises:

a reservoir of pressurized gas; and a valve interposed between the reservoir of pressurized gas and the inlet of the convergent to controllably supply pressurized gas from the reservoir to the inlet of the convergent and thereby generate the high velocity jet of gas.

13. A needleless syringe for injecting a liquid substance as defined in claim 8, wherein the high velocity jet of gas comprises inert gas.

14. A needleless syringe for injecting a liquid substance as defined in claim 8, wherein the perforated membrane comprises at least one micro-orifice and the source of pressurization comprises a pressurized gas supply connected to the reservoir of the liquid substance to supply pressurized gas to the reservoir and force the liquid substance through the perforated membrane to thereby generate the droplets of the liquid substance supplied in the channel and, therefore, in the high velocity jet of gas.

15. A needleless syringe for injecting a liquid substance as defined in claim 14, wherein the pressurized gas supply comprises:

a reservoir of pressurized gas; and a valve interposed between the reservoir of pressurized gas and the reservoir of the liquid substance to controllably supply pressurized gas from the reservoir of pressurized gas to the reservoir of the liquid substance to thereby force the liquid substance through the perforated membrane and thereby generate the droplets of the liquid substance supplied in the channel and, therefore, in the high velocity jet of gas.

16. A needleless syringe for injecting a liquid substance as defined in claim 14, wherein the perforated membrane comprises a metallic or polymeric membrane provided with the at least one micro-orifice.

17. A needleless syringe for injecting a liquid substance as defined in claim 14, wherein the generator of the high velocity jet of gas comprises:

a convergent-divergent comprising a throat through which the high velocity jet of gas travels; wherein:

the perforated membrane is interposed between the reservoir of the liquid substance and the throat of the convergent-divergent.

18. A needleless syringe for injecting a liquid substance as defined in claim 8, wherein the generator of the high velocity jet of gas comprises:

a pressurized gas supply;

a convergent-divergent having an inlet; and an intermediate chamber interposed between the pressurized gas supply of the generator of the high velocity jet of gas and the inlet of the convergent-divergent.

19. A needleless syringe for injecting a liquid substance as defined in claim 18, wherein the generator of the high velocity jet of gas further comprises:

a first valve interposed between the pressurized gas supply of the generator of the jet of gas and the intermediate chamber to control supply of pressurized gas from said pressurized gas supply to the intermediate chamber; and a second valve interposed between the intermediate chamber and the inlet of the convergent-divergent to control supply of pressurized gas from the intermediate chamber to the convergent-divergent.

20. A needleless syringe for injecting a liquid substance as defined in claim 8, wherein the generator of the high velocity jet of gas comprises:

a pressurized gas supply;

a convergent having an inlet; and an intermediate chamber interposed between the pressurized gas supply of the generator of the high velocity jet of gas and the inlet of the convergent.

21. A needleless syringe for injecting a liquid substance as defined in claim 20, wherein the generator of the high velocity jet of gas comprises:

a first valve interposed between the pressurized gas supply of the generator of the high velocity jet of gas and the intermediate chamber to control supply of pressurized gas from said pressurized gas supply to the intermediate chamber; and a second valve interposed between the intermediate chamber and the inlet of the convergent to control supply of pressurized gas from the intermediate chamber to the convergent.

22. A needleless syringe for injecting a liquid substance as defined in claim 14, wherein the generator of the droplets of the liquid substance further comprises:

an intermediate chamber interposed between the pressurized gas supply and the reservoir of the liquid substance.

23. A needleless syringe for injecting a liquid substance as defined in claim 22, wherein the generator of the droplets of the liquid substance further comprises:
   a first valve interposed between the pressurized gas supply and the intermediate chamber to control supply of pressurized gas from the pressurized gas supply to the intermediate chamber; and
   a second valve interposed between the intermediate chamber and the reservoir of liquid substance to control supply of pressurized gas from the intermediate chamber to the reservoir of the liquid substance.

24. A needleless syringe for injecting a liquid substance as defined in claim 23, wherein the reservoir of the liquid substance comprises:
   a liquid chamber adjacent to the perforated membrane for containing the liquid substance;
   a gas-tight chamber; and
   a slidable piston interposed between the liquid chamber and the gas-tight chamber; wherein:
      the second valve is interposed between the intermediate chamber and the gas-tight chamber to control supply of pressurized gas from the intermediate chamber to the gas-tight chamber; and
      the supply of pressurized gas to the gas-tight chamber applies a pressure on the slidable piston to compress the liquid substance in the liquid chamber and force the liquid substance through the perforated membrane to thereby generate the droplets of the liquid substance supplied in the high velocity jet of gas.

25. A needleless syringe for injecting a liquid substance as defined in claim 10, wherein the valve is an electronic valve.

26. A needleless syringe for injecting a liquid substance as defined in claim 10, wherein the valve is a mechanical valve comprising elements selected from the group consisting of pistons, springs and plungers.

27. A method for needleless injection of a liquid substance into a target biological tissue, the method comprising:
   generating droplets of the liquid substance;
   accelerating the droplets of the liquid substance at a velocity sufficiently high to inject the droplets of the liquid substance into the target biological tissue; and
   directing the droplets of the liquid substance toward a surface of the target biological tissue at the sufficiently high velocity to inject the droplets of the liquid substance into the target biological tissue;
   wherein generating the droplets of the liquid substance comprises injecting a pressurized gas from a pressurized source into a reservoir containing the liquid substance to force the liquid substance from the liquid reservoir through at least one micro-orifice of a perforated membrane to thereby produce a jet of the liquid substance, wherein the jet of the liquid substance transforms into a stream of the droplets.

28. A needleless syringe for injecting a liquid substance into a target biological tissue, comprising:
   a generator of droplets of the liquid substance; and
   a droplet accelerator for accelerating the droplets of the liquid substance toward a surface of the target biological tissue in order to inject the accelerated droplets into the target biological tissue; and
   wherein the generator of droplets comprises:
      a reservoir of the liquid substance to be injected;
      a perforated membrane comprising at least one micro-orifice through which the liquid substance from the reservoir is supplied;
      a source of pressurized gas; and
      a valve for connecting the source of pressurized gas to the reservoir of the liquid substance, wherein opening of the valve causes pressurized gas from the source to be supplied to the reservoir for pressurizing the reservoir of the liquid substance and forcing the liquid substance through the at least one micro-orifice of the perforated membrane to thereby produce a jet of the liquid substance, wherein the jet of the liquid substance transforms into a stream of the droplets.

29. A method for needleless injection of a liquid substance into a target biological tissue, the method comprising:
   generating droplets of the liquid substance;
   accelerating the droplets of the liquid substance, at a velocity sufficiently high to inject the droplets of the liquid substance into the target biological tissue; and
   directing the droplets of the liquid substance toward a surface of the target biological tissue at the sufficiently high velocity to inject the droplets of the liquid substance into the target biological tissue;
   wherein generating the droplets of the liquid substance comprises:
      supplying pressurized gas to a gas-tight chamber;
      applying, by means of the pressurized gas in the gas-tight chamber, a pressure to a slidable piston interposed between the gas-tight chamber and a reservoir of the liquid substance to be injected;
      compressing the liquid substance in the liquid reservoir by means of the pressure applied to the slidable piston to force the liquid substance through at least one micro-orifice of a perforated membrane to thereby produce a jet of the liquid substance, wherein the jet of the liquid substance transforms into a stream of the droplets.

30. A needleless syringe for injecting a liquid substance into a target biological tissue, comprising:
   a generator of droplets of the liquid substance; and
   a droplet accelerator for accelerating the droplets of the liquid substance toward a surface of the target biological tissue in order to inject the accelerated droplets into the target biological tissue; and
   wherein the generator of droplets comprises:
      a source of pressurized gas;
      a gas-tight chamber connected to the source of pressurized gas through a valve;
      a reservoir of the liquid substance to be injected;
      a slidable piston interposed between the liquid reservoir and the gas-tight chamber;
      a perforated membrane comprising at least one micro-orifice through which the liquid substance from the reservoir is supplied; and
   wherein opening of the valve to supply pressurized gas from the source to the gas-tight chamber applies a pressure on the slidable piston to compress the liquid substance in the liquid reservoir and force the liquid substance through the at least one micro-orifice of the perforated membrane to thereby produce a jet of the liquid substance, wherein the jet of the liquid substance transforms into a stream of the droplets.

31. A method for needleless injection of a liquid substance into a target biological tissue, the method comprising:
   generating a high velocity jet of gas;
   generating droplets of the liquid substance;
   supplying and conveying the droplets of the liquid substance into the high velocity jet of gas; and guiding the high velocity jet of gas through a channel toward a surface of the target biological tissue for injecting the conveyed droplets of the liquid substance into the target biological tissue;

wherein generating the droplets of the liquid substance comprises containing the liquid substance in a cylindrical reservoir positioned coaxial within the channel, the cylindrical reservoir comprising a downstream perforated membrane and an upstream slidable piston and the liquid substance being contained in the cylindrical reservoir between the perforated membrane and the slidable piston;

wherein generating the high velocity jet of gas comprises releasing upstream of the channel pressurized gas to produce the high velocity jet of gas; and wherein pressurized gas released in the channel applies a pressure to the slidable piston to compress the liquid substance in the liquid reservoir and force the liquid substance through the perforated membrane to thereby produce a jet of the liquid substance, the jet of the liquid substance transforming into a stream of the droplets supplied in the high velocity jet of gas.

32. A needleless syringe for injecting a liquid substance into a target biological tissue, the syringe comprising:

a generator of high velocity jet of gas;

a generator of droplets of the liquid substance having an outlet for supplying the droplets of the liquid substance into the high velocity jet of gas whereby the droplets of the liquid substance are conveyed within the high velocity jet of gas; and a channel for guiding the high velocity jet of gas toward a surface of the target biological tissue to thereby inject the conveyed droplets of the liquid substance into the target biological tissue;

wherein the generator of the droplets of the liquid substance comprises a cylindrical reservoir containing the liquid substance and positioned coaxial within the channel, the cylindrical reservoir comprising a downstream perforated membrane and an upstream slidable piston and the liquid substance being contained in the cylindrical reservoir between the perforated membrane and the slidable piston;

wherein the generator of the high velocity jet of gas comprises a source of pressurized gas positioned upstream of the channel to release in the channel pressurized gas to produce the high velocity jet of gas; and wherein pressurized gas released form the source applies a pressure to the slidable piston to compress the liquid substance in the liquid reservoir and force the liquid substance through the perforated membrane to thereby produce a jet of the liquid substance, the jet of the liquid substance transforming into a stream of the droplets supplied in the high velocity jet of gas.

* * * * *